US00PP29096P2

(12) United States Plant Patent
Hofmann

(10) Patent No.: US PP29,096 P2
(45) Date of Patent: Mar. 13, 2018

(54) ***MANDEVILLA* PLANT NAMED 'INMANREDEEP'**

(50) Latin Name: *Mandevilla hybrida*
Varietal Denomination: Inmanredeep

(71) Applicant: Birgit Hofmann, Rudesheim am Rhein (DE)

(72) Inventor: Birgit Hofmann, Rudesheim am Rhein (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 0 days.

(21) Appl. No.: 15/330,327

(22) Filed: Sep. 6, 2016

(51) Int. Cl.
*A01H 5/02* (2006.01)

(52) U.S. Cl.
USPC ..... Plt./232

(58) Field of Classification Search
USPC ..... Plt./232
See application file for complete search history.

(56) References Cited

PUBLICATIONS

UPOV hit on *Mandevilla* plant named 'Inmanredeep', QZ PBR 20161661, filed Jul. 1, 2016.*

* cited by examiner

*Primary Examiner* — Anne M Grunberg
(74) *Attorney, Agent, or Firm* — C. A. Whealy

(57) ABSTRACT

A new and distinct cultivar of *Mandevilla* plant named 'Inmanredeep', characterized by its upright and vining plant habit; moderately vigorous growth habit; freely branching habit; moderately glossy dark green-colored leaves; freely flowering habit; and dark red-colored flowers that resist fading and sun scald.

2 Drawing Sheets

Botanical designation: *Mandevilla hybrida.*

Cultivar denomination: 'INMANREDEEP'.

BACKGROUND OF THE INVENTION

The present invention relates to a new and distinct cultivar of *Mandevilla* plant, botanically known as *Mandevilla hybrida* and hereinafter referred to by the name 'Inmanredeep'.

The new *Mandevilla* plant is a product of a planned breeding program conducted by the Inventor in Johannesburg, South Africa and Heidesheim, Germany. The objective of the breeding program is to create new freely branching *Mandevilla* plants that flower freely and have attractive flowers that resist fading and sun scald.

The new *Mandevilla* plant originated from a cross-pollination conducted by the Inventor in Johannesburg, South Africa in November, 2010 of a proprietary selection of *Mandevilla hybrida* identified as code number D09-1078-4, not patented, as the female, or seed parent with a proprietary selection of *Mandevilla hybrida* identified as code number D09-1063-2, not patented, as the male, or pollen, parent. The new *Mandevilla* plant was discovered and selected by the Inventor as a single flowering plant from within the progeny of the stated cross-pollination in a controlled greenhouse environment in Heidesheim, Germany in June, 2012.

Asexual reproduction of the new *Mandevilla* plant by cuttings in a controlled greenhouse environment in Heidesheim, Germany, since June, 2012 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inmanredeep'. These characteristics in combination distinguish 'Inmanredeep' as a new and distinct *Mandevilla* plant:

1. Upright and vining plant habit.
2. Moderately vigorous growth habit.
3. Freely branching habit.
4. Moderately glossy dark green-colored leaves.
5. Freely flowering habit.
6. Dark red-colored flowers that resist fading and sun scald.

Plants of the new *Mandevilla* can be compared to plants of the female parent selection. Plants of the new *Mandevilla* differ primarily from plants of the female parent selection in the following characteristics:

1. Plants of the new *Mandevilla* are not as vigorous and dense as plants of the female parent selection.
2. Plants of the new *Mandevilla* have smaller leaves than plants of the female parent selection.
3. Plants of the new *Mandevilla* have smaller flowers than plants of the female parent selection.
4. Plants of the new *Mandevilla* and the female parent selection differ in flower color as plants of the female parent selection have light pink-colored flowers.

Plants of the new *Mandevilla* can be compared to plants of the male parent selection. Plants of the new *Mandevilla* differ primarily from plants of the male parent selection in the following characteristics:

1. Plants of the new *Mandevilla* are not as compact as plants of the male parent selection.
2. Plants of the new *Mandevilla* have larger leaves than plants of the male parent selection.
3. Plants of the new *Mandevilla* flower later than plants of the male parent selection.
4. Plants of the new *Mandevilla* and the male parent selection differ in flower color as flowers of plants of the male parent have pink-colored flowers.

Plants of the new *Mandevilla* can also be compared to plants of *Mandevilla amabilis*×*Mandevilla boliviensis* 'Sunmandecrim', disclosed in U.S. Plant Pat. No. 15,539. In side-by-side comparisons plants of the new *Mandevilla* differ primarily from plants 'Sunmandecrim' in the following characteristics:

1. Plants of the new *Mandevilla* produce rooted young plants ten days earlier than plants of 'Sunmandecrim'.
2. Plants of the new *Mandevilla* are bushier and denser than plants of 'Sunmandecrim'.
3. Flowers of plants of the new *Mandevilla* are more open than flowers of plants of 'Sunmandecrim'.
4. Flowers of plants of the new *Mandevilla* do not sun scald under high light conditions whereas flowers of plants of 'Sunmandecrim' sun scald under high light conditions.

Plants of the new *Mandevilla* can also be compared to plants of *Mandevilla sanderi* 'Rio Red', not patented. In side-by-side comparisons plants of the new *Mandevilla* differ primarily from plants 'Rio Red' in the following characteristics:

1. Plants of the new *Mandevilla* produce rooted young plants ten days earlier than plants of 'Rio Red'.
2. Plants of the new *Mandevilla* are more freely branching than plants of 'Rio Red'.
3. Plants of the new *Mandevilla* have larger flowers than plants of 'Rio Red'.
4. Flower color of plants of the new *Mandevilla* does not fade whereas flower color of plants of 'Rio Red' fades.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Inmanredeep' grown in a container.

The photograph on the second sheet is a close-up view of a typical flowering plant of 'Inmanredeep'.

DETAILED BOTANICAL DESCRIPTION

The aforementioned photographs and following observations, measurements and values describe plants grown during the late spring and early summer in 9.5-cm containers in a polyethylene-covered greenhouse in Almeria, Spain and under cultural practices typical of *Mandevilla* commercial production. During the production of the plants, day temperatures ranged from 20° C. to 35° C. and night temperatures ranged from 20° C. to 25° C. Plants were 15 weeks old when the photographs and description were taken. In the following description, color references are made to The Royal Horticultural Society Colour Chart, 2015 Edition, except where general terms of ordinary dictionary significance are used.

Botanical classification: *Mandevilla hybrida* 'Inmanredeep'.

Parentage:

*Female, or seed, parent.*—Proprietary selection of *Mandevilla hybrida* identified as code number D09-1078-4.

*Male, or pollen, parent.*—Proprietary selection of *Mandevilla hybrida* identified as code number D09-1063-2.

Propagation:

*Type.*—By vegetative cuttings.

*Time to initiate roots, summer.*—About three weeks at temperatures ranging from 20° C. to 35° C.

*Time to initiate roots, winter.*—About three weeks at temperatures ranging from 20° C. to 25° C.

*Time to produce a rooted young plant, summer.*—About 20 to 25 days at temperatures ranging from 20° C. to 35° C.

*Time to produce a rooted young plant, winter.*—About 25 to 30 days at temperatures ranging from 20° C. to 25° C.

*Root description.*—Thick, fleshy; typically white in color, actual color of the roots is dependent on substrate composition, water quality, fertilizers, substrate temperature and physiological age of roots.

*Rooting habit.*—Low branching; medium density.

Plant description:

*Plant and growth habit.*—Upright and vining plant habit; moderately vigorous growth habit.

*Plant height.*—About 46.5 cm.

*Plant diameter (spread).*—About 55.5 cm.

*Lateral branch description.*—Branching habit: Freely branching habit with about four lateral branches and about 24 secondary branches developing per plant; pinching enhances lateral branch development. Length: About 19.3 cm. Diameter: About 2.5 mm. Internode length: About 4.6 cm. Strength: Strong. Texture and luster: Smooth, glabrous; glossy; becoming woody with development. Color, developing: Close to 144B. Color, developed: Close to 144A; when woody, close to N199C to N199D.

Leaf description:

*Arrangement.*—Opposite, simple.

*Length.*—About 6.3 cm.

*Width.*—About 4 cm.

*Shape.*—Obovate to broadly obovate.

*Apex.*—Short apiculate.

*Base.*—Obtuse to truncate.

*Margin.*—Entire.

*Texture and luster, upper surface.*—Smooth, glabrous; moderately glossy.

*Texture and luster, lower surface.*—Smooth, glabrous; slightly glossy.

*Venation pattern.*—Pinnate.

*Color.*—Developing leaves, upper surface: Slightly darker than 143A. Developing leaves, lower surface: Close to between 144B and 146C. Full expanded leaves, upper surface: Darker than between N137A and 147A; venation, close to 143B. Fully expanded leaves, lower surface: Close to 146B; venation, close to 145B.

*Petioles.*—Length: About 9 mm. Diameter: About 2 mm. Strength: Moderately strong. Texture and luster, upper and lower surfaces: Smooth, glabrous; moderately glossy. Color, upper surface: Close to 144B. Color, lower surface: Close to 145B.

Flower description:

*Flower type and flowering habit*.—Single salverform flowers arranged in axillary cymes; flowers star-shaped and face mostly outwardly; freely flowering habit with about five flowers developing per inflorescence and about 95 flowers developing per plant during the flowering season.

*Natural flowering season*.—Plants flower continuously from spring into the autumn in Spain.

*Flower longevity on the plant*.—About ten days; flowers not persistent.

*Fragrance*.—None detected.

*Inflorescence height*.—About 10.9 cm.

*Inflorescence diameter*.—About 12.1 cm.

*Flower buds*.—Length: About 5.5 cm. Diameter: About 8 mm. Shape: Narrowly oblanceolate. Texture and luster: Smooth, glabrous; slightly glossy. Color: Close to 187B and 53C; towards the base, close to 145A and 145B.

*Flowers*.—Appearance: Flared trumpet, corolla fused and five-parted. Diameter: About 8.5 cm. Depth (length): About 8 cm. Throat diameter: About 1.5 cm. Tube length: About 5.3 cm. Tube diameter: Proximally, about 4 mm; distally, about 1.6 cm.

*Corolla*.—Quantity and arrangement: Five petals arranged in a single whorl; lower 55% portion of the petals are fused into a tube. Petal length: About 9.5 cm. Petal width: About 3.5 cm. Petal shape and appearance: Roughly spatulate. Petal apex: Non-symmetrically apiculate. Petal margin: Entire; slightly undulate. Petal texture and luster, upper surface: Smooth, glabrous; velvety; matte. Petal texture and luster, lower surface: Smooth, glabrous; velvety; moderately glossy. Throat and tube texture: Smooth, glabrous. Color: Petal, when opening, upper surface: Darker and more intense than N45A. Petal, when opening, lower surface: Close to between 53A and 185A. Petal, fully opened, upper surface: Darker and more intense than 53A; venation, similar to lamina; color does not fade with development; flowers do not sun scald under high light conditions. Petal, fully opened, lower surface: Close to between 53A and 185A; color does not fade with development. Throat: Close to N45A; venation, close to 31A. Tube: Close to N144A; venation, close to N144A.

*Corona*.—Quantity and arrangement: Five sepals arranged in a single whorl. Sepal length: About 8 mm. Sepal width: About 2 mm. Sepal shape: Narrowly deltoid. Sepal apex: Narrowly acute. Sepal base: Broadly cuneate. Sepal margin: Entire. Sepal texture and luster, upper surface: Smooth, glabrous; moderately glossy. Sepal texture and luster, lower surface: Smooth, glabrous; matte. Sepal color: Immature, upper and lower surfaces: Close to 145C; at the apex, close to 179A. Mature, upper and lower surfaces: Close to 145C to 145D.

*Peduncles*.—Length: About 5.8 cm. Diameter: About 2 mm. Strength: Strong. Aspect: About 30° from lateral branch axis. Texture and luster: Smooth, glabrous; glossy. Color: Close to 143C.

*Pedicels*.—Length: About 1.3 cm. Diameter: About 2 mm. Strength: Strong. Aspect: About 25° from peduncle axis. Texture and luster: Smooth, glabrous; moderately glossy. Color: Close to 145A.

*Reproductive organs*.—Stamens: Quantity and arrangement: Typically five; basifixed; anthers connivent. Filament length: About 1 mm. Filament color: Close to 151D. Anther shape: Narrowly oblong. Anther size: About 8 mm by 1.5 mm. Anther color: Close to 11B to 11C. Pollen amount: None observed. Pistils: Quantity: Typically one. Pistil length: About 2.3 cm. Style length: About 1.9 cm. Style color: Close to 145D. Stigma diameter: About 2 mm. Stigma shape: Club-shaped. Stigma color: Close to 146C. Ovary color: Close to 144A.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be suitable for USDA Hardiness Zones 9 to 13.

It is claimed:

1. A new and distinct *Mandevilla* plant named 'Inmanredeep' as illustrated and described.

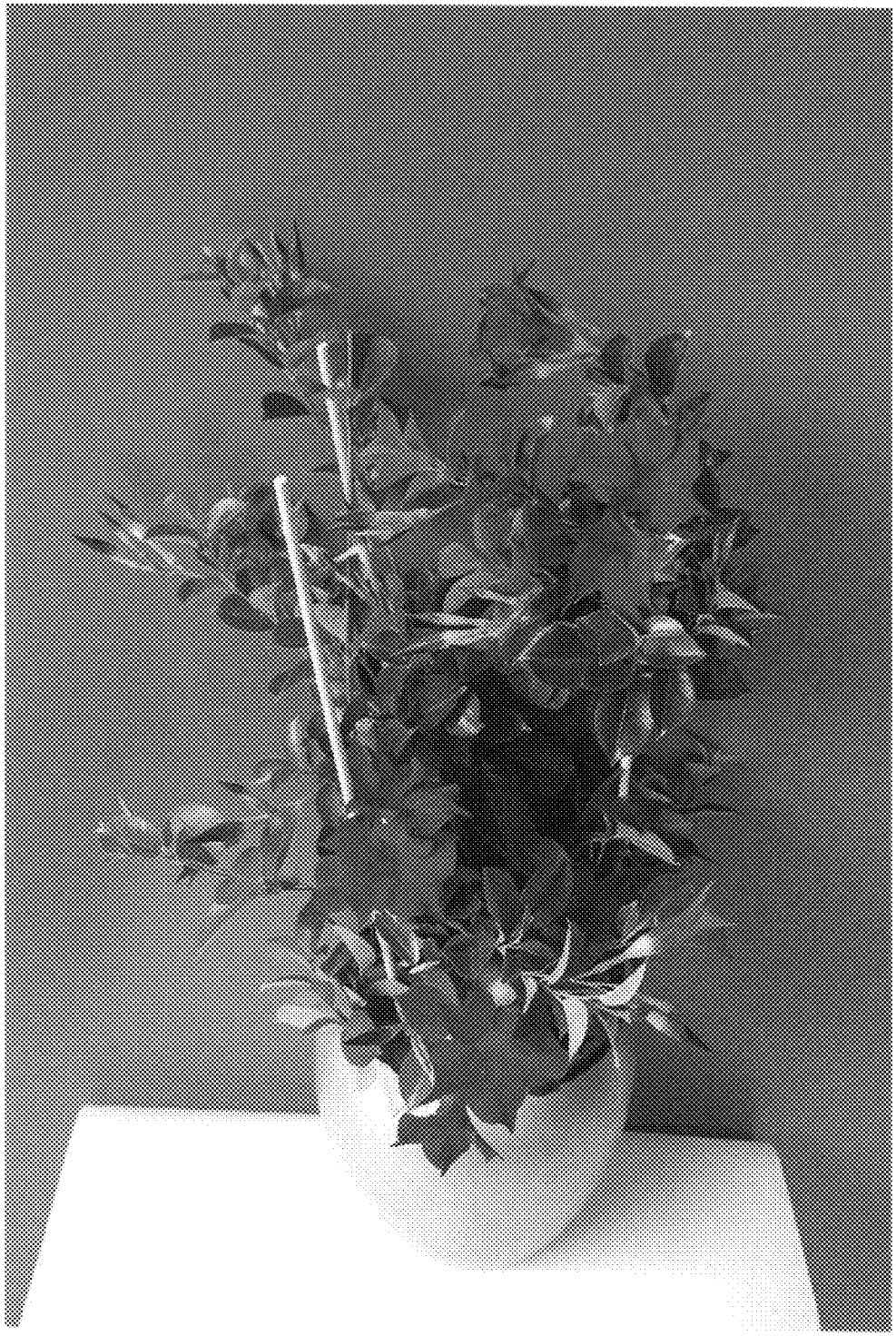

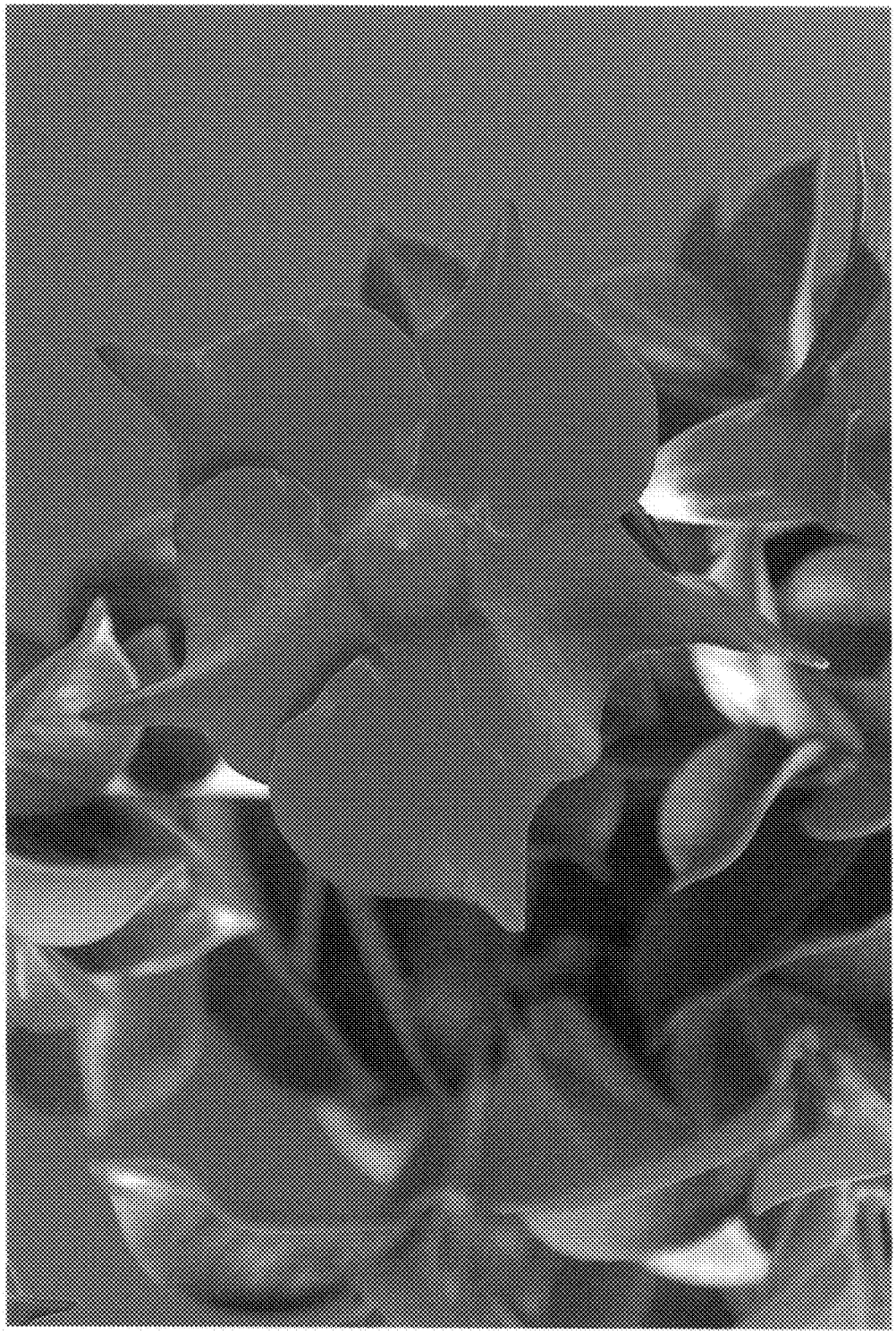

* * * * *